United States Patent [19]

Rebsdat et al.

[11] Patent Number: 4,478,948
[45] Date of Patent: Oct. 23, 1984

[54] PROCESS FOR IMPROVING THE ACTIVITY OF USED SUPPORTED SILVER CATALYSTS

[75] Inventors: Siegfried Rebsdat, Burg; Sigmund Mayer, Burgkirchen; Josef Alfranseder, Hofschallern, all of Fed. Rep. of Germany

[73] Assignee: Hoechst Aktiengesellschaft, Frankfurt am Main, Fed. Rep. of Germany

[21] Appl. No.: 520,142

[22] Filed: Aug. 4, 1983

[30] Foreign Application Priority Data

Aug. 7, 1982 [DE] Fed. Rep. of Germany ....... 3229541

[51] Int. Cl.³ .................... B01J 23/96; C07D 301/10
[52] U.S. Cl. ........................................ 502/25; 502/33; 549/534
[58] Field of Search .................................... 502/25, 33

[56] References Cited

U.S. PATENT DOCUMENTS

| 3,962,136 | 6/1976 | Nielsen et al. | 252/454 |
| 4,033,903 | 7/1977 | Maxwell | 252/476 |
| 4,051,068 | 9/1977 | Rebsdat et al. | 252/412 |
| 4,123,385 | 10/1978 | Rebsdat et al. | 252/414 |
| 4,125,480 | 11/1978 | Maxwell | 502/33 |
| 4,177,169 | 12/1979 | Rebsdat et al. | 252/476 |
| 4,186,106 | 1/1980 | Rebsdat et al. | 252/414 |
| 4,278,562 | 7/1981 | Mross et al. | 252/430 |
| 4,335,014 | 6/1982 | Alfranseder et al. | 252/412 |

Primary Examiner—P. E. Konopka
Attorney, Agent, or Firm—Curtis, Morris & Safford

[57] ABSTRACT

A method for improving the activity of a used supported silver catalyst, used for the manufacture of ethylene oxide by reaction of ethylene with oxygen or air, which method consists essentially of:

(a) impregnating said used catalyst at a temperature from 80° C. to 150° C. and for 0.75 hour to 10 hours with an impregnating solution containing water, a water-miscible organic solvent selected from the group consisting of methanol, ethanol, propanol, and isopropanol, at least one compound of cesium, rubidium, or of cesium and rubidium in an amount providing from 50 mg to 1000 mg per kilogram of solution, said solution containing from 5 to 50 percent by weight of water;

(b) separating the impregnated catalyst from excess impregnating solution; and (c) drying the impregnated catalyst.

5 Claims, No Drawings

PROCESS FOR IMPROVING THE ACTIVITY OF USED SUPPORTED SILVER CATALYSTS

The invention relates to a process for improving the activity of used supported silver catalysts for the manufacture of ethylene oxide by reaction of ethylene with molecular oxygen or air.

Silver catalysts, the manufacture of which has been known for a long time and has been described in a variety of patent specifications, are employed for the manufacture of ethylene oxide by oxidation of ethylene with oxygen or air. A whole series of large-scale industrial plants for the manufacture of ethylene oxide use the silver catalyst process. In this process, only a fraction of the ethylene employed is generally converted. On the supporting material, impregnated with silver, the ethylene which is reacted is converted by means of oxygen predominantly to ethylene oxide; the remainder is transformed virtually completely into carbon dioxide and water.

In the course of time, a very wide variety of silver catalyst has been developed, specifically with the aim of increasing the selectivity with respect to the preferred formation of ethylene oxide and of repressing the formation of $CO_2$ and water.

With rising prices and increasing scarcity of raw materials, increased selectivity of catalysts acquires a particular economic importance. In principle, two routes which enable supported silver catalysts having an increased selectivity to be obtained have been described in the literature in recent years. One route is based on the development of new supported silver catalysts which differ from the older catalysts particularly in the silver deposited having a special morphology, in a special support material or in selected promoters. For example, German Offenlegungsschrift No. 2,300,512 describes a supported silver catalyst which is obtained by depositing 0.0004 to 0.0027 g equivalents of a potassium, rubidium or cesium compound per kg of catalyst on aluminum oxide from an aqueous solution, simultaneously with the silver.

The other route for the preparation of supported silver catalysts having an increased selectivity is based on the fact that the selectivity of a catalyst which is in itself ready for use is substantially improved by an after-treatment. In this route, the starting material is a supported silver catalyst which has already been utilized for the manufacture of ethylene oxide for periods of varying length. The after-treatment is as follows: The used catalyst is impregnated with a solution consisting of water, a water-miscible organic solvent and at least one cesium and/or rubidium compound in an amount of from 50 to 1,000, preferably 80 to 500, mg, especially 100 to 400 mg of cesium and/or rubidium per kg of solution, the excess impregnating solution is separated, and the impregnated catalyst is dried. The catalyst so treated is then used again for the manufacture of ethylene oxide by reaction of ethylene with molecular oxygen or air. Such processes for improving the selectivity of used supported silver catalysts are described in German Pat. Nos. 2,519,599, 2,611,856, 2,636,680 and 2,649,359, and in German Offenlegungsschriften Nos. 2,712,785, 2,740,480, 2,746,976, 2,751,767, 2,820,520 and 2,938,245.

In all these known processes for improving the selectivity of used catalysts, the temperature at which the used catalyst is treated with the impregnating (regenerating) solution is considered to be not critical. In nearly all cases the treatment is carried out at room temperature, with the exception of the process of German Offenlegungsschrift No. 2,938,245, where the catalyst is impregnated at a temperature of up to 30° C. (see Examples). However, even in this latter case the impregnation temperature is considered obviously to be without importance with respect to improvement of selectivity.

Furthermore, no special importance is attached to the impregnation (contact) time, that is, the time within which the catalyst to be impregnated remains in contact with the impregnating liquid; it is subject to practical considerations only. In any event, as far as the time is indicated, contact times of from 3 to 120, preferably 5 to 20, minutes are indicated (see German Pat. Nos. 2,636,680 and 2,649,359 and German Offenlegungsschrift No. 2,740,480).

Likewise, no special importance is attached to the amount of water in the impregnating solution with respect to the successful after-treatment of a used supported silver catalyst. Obviously, the amount of water serves only as solubilizer for the cesium and rubidium compound used in the water-miscible organic solvent. For example, the solubility of some cesium compounds in pure methanol is so low that the required cesium concentration in the impregnating solution is attained only with difficulty in certain cases. For these reasons only, the impregnating solution contains up to 40 weight % of water (see for example German Pat. Nos. 2,636,680 and 2,649,359 and German Offenlegungsschrift No. 2,712,785 p. 11).

In some of the known processes for reactivating used supported silver catalysts, it is recommended to add special oxygen and/or nitrogen compounds to the impregnating solution containing cesium and/or rubidium compounds in order to obtain the intended results (see German Offenlegungsschriften Nos. 2,751,767 and 2,820,520), or to wash the catalyst before the impregnation (see German Offenlegungsschriften Nos. 2,740,480, 2,746,967 and 2,938,245).

According to the state of art with respect to improvement of the activity of used supported silver catalysts, therefore, no critical importance has been attached either to the impregnation temperature, or to the impregnation time, or to the water content of the impregnating solution. On the contrary, in order to attain a high selectivity in the impregnation process based on solutions containing cesium and/or rubidium, the use of additional specific compounds in the impregnating solution, or a washing of the used catalyst has been recommended. These operations are complicated and time-consuming, and in case of the washing, even an additional process step is required.

It is the object of the invention to provide a novel process for improving the activity of used supported silver catalysts which is relatively simple and permits attaining an especially high efficiency.

Surprisingly, it has been found that in the known reactivation of used supported silver catalysts by treatment with an impregnating solution consisting of water, a water-miscible organic solvent and at least one cesium compound, rubidium compound or cesium and rubidium compound in an amount of from 50 to 1,000, preferably 80 to 500, and especially 100 to 400, mg of cesium, rubidium or cesium and rubidium per kg of solution, the impregnation temperature, the impregantion time and the amount of water in the impregnating solution are critical for attaining a high degree of reactivation, and that the selectivity is greatly increased when impregnating at elevated temperature, the impregnation time is at least 0.3 hour, and the impregnating solution has a water content of at least 5 weight percent relative to the weight of the solution.

The process of the invention for improving the activity of used supported silver catalysts for the manufacture of ethylene oxide by reaction of ethylene with molecular oxygen or air, in which the used catalyst is impregnated with a solution consisting of water, a water-miscible organic solvent and at least one cesium and/or rubidium compound in an amount of from 50 to 1,000 mg of cesium and/or rubidium per kg of solution, the excess impregnating solution is separated and the impregnated catalyst is dried, comprises impregnating at a temperature of from 60° C. to 200° C., the impregnation time being at least 0.3 hour, and the impregnating solution containing from 5 to 50 weight percent of water, relative to the weight of the solution.

The impregnation temperature is preferably from 80° C. to 150° C., especially 90° C. to 130° C.

The impregnation time is generally from 0.3 to 20, preferably 0.75 to 10, especially 1 to 3 hours.

The water content of the impregnating solution is preferably from 10 to 40, especially 10 to 30, weight percent relative to the weight of the solution.

Preparation of the impregnating solution, impregnation of the used silver catalyst, separation of the excess impregnating solution after impregnation, and drying of the impregnated catalyst as such are known from the cited publications. Thus, the impregnating solution is obtained in simple manner by mixing the individual components. Suitable water-miscible organic solvents are aliphatic ketones having 3 to 10 carbon atoms and/or aliphatic alcohols having 1 to 6 carbon atoms. Preferred are aliphatic ketones having 3 to 6 carbon atoms such as acetone, methylethylketone, ethylpropylketone or dipropylketone, and aliphatic alcohols having 1 to 3 carbon atoms such as methanol, ethanol, propanol or isopropanol. The aliphatic alcohols are especially preferred.

Suitable cesium and rubidium compounds are the (water-soluble) salts and hydroxides of cesium and rubidium. Appropriate salts (inorganic or organic) are the nitrates, carbonates, bicarbonates, formates, acetates, oxalates or lactates; the nitrates and acetates being preferred for simply practical reasons only.

The nature of the cesium and/or rubidium compound is not decisive for the effect according to the invention.

The anion in the cesium and rubidium salt is also of no importance.

Either one or more cesium or rubidium compounds can be employed; mixtures of cesium and rubidium compounds are also suitable.

For impregnating the used supported silver catalyst according to the process of the invention, a solution is generally used which consists of 5 to 50 weight % of water, 50 to 1,000 mg of cesium and/or rubidium per kg of solution in the form of a (water-soluble) salt or hydroxide of cesium and/or rubidium, the remainder (to 100 weight percent of solution) being a water-miscible organic solvent, preferably an aliphatic alcohol having 1 to 3 carbon atoms and/or an aliphatic ketone having 3 to 6 carbon atoms.

Preferably, an impregnating solution is used which consists of 10 to 40 weight % of water, 80 to 500 mg of cesium and/or rubidium per kg of solution in the form of a (water-soluble) salt or hydroxide of cesium and/or rubidium, the remainder being a water-miscible organic solvent, preferably an aliphatic alcohol having 1 to 3 carbon atoms and/or an aliphatic ketone having 3 to 6 carbon atoms.

Particularly preferred is an impregnation solution which consists of 10 to 30 weight % of water, 100 to 400 mg of cesium and/or rubidium per kg of solution in the form of a (water-soluble) salt or hydroxide of cesium and rubidium, the remainder being a water-miscible solvent, preferably an aliphatic alcohol having 1 to 3 carbon atoms and/or an aliphatic ketone having 3 to 6 carbon atoms.

The amount of impregnating solution is generally chosen such that an excess by volume, relative to the silver catalyst to be impregnated, is present. Generally, a 0.5- to 3-fold, preferably a 1- to 2-fold volume of impregnating liquid, relative to the volume of the catalyst to be impregnated, is used.

According to an advantageous method the impregnation is carried out as follows: the impregnating solution is poured over the catalyst in a receptacle (autoclave), catalyst and impregnating liquid are heated to the temperature according to the invention, optionally while stirring, and then maintained at this temperature during a time in accordance with the invention.

According to another advantageous method, so-called flooding, the impregnating solution is passed over the catalyst arranged as a fixed bed in one or more tubes. This latter method is particularly advisable in large plants in which the catalyst to be regenerated is already present in the tubes of the reactor. The pouring over (flooding) can be carried out once or several times (using the impregnating liquid which has been separated or a freshly prepared impregnating liquid), continuously or batchwise.

In continuous impregnation, the impregnating solution is pump-circulated while maintaining an impregnation time according to the invention; in the batchwise process the solution is kept for this time in the tubes which are accordingly closed. In the case of flooding, too, it is advisable to attain and adjust the impregnation temperature according to the invention by heating catalyst and impregnating liquid to this temperature. It stands to reason that in the impregnation according to the invention, due to the elevated impregnation temperature, pressures occur which correspond to the vapor pressure of the impregnating liquids used.

After the impregnation, the excess impregnating liquid is separated from the catalyst, either by pouring-off, filtering-off, centrifugation, or in the case of flooding by simply allowing it to drain.

After separation from the excess impregnating liquid, the impregnated catalyst which is still more or less moist is dried, generally at a temperature from 20° C. to 150° C., preferably 50° C. to 120° C. The solvent may be evaporated, for example by means of shelf driers, rotary tube furnaces, or by passing hot inert gases such as nitrogen, air and/or carbon dioxide over it. The temperature is generally chosen in dependence on the boiling point of the solvent of the impregnating liquid. According to a preferred mode of operation, the catalyst is dried in the presence of inert gas at a temperature of from 50° C. to 120° C.

After drying, the catalyst is ready for use and improved with respect to its activity.

The process according to the invention is independent of the nature of the supported silver catalyst itself. Any silver catalyst which is suitable and used for the direct oxidation of ethylene to ethylene oxide by means of molecular oxygen or air can be used in the process according to the invention. Silver catalysts for the direct oxidation of ethylene to ethylene oxide by means of molecular oxygen or air are described exhaustively in the literature, as is the direct oxidation process itself, for example in U.S. Pat. Nos. 2,615,899, 3,899,445 and 3,962,136. The silver catalysts in question generally consist of silver in an amount from 3 to 20, preferably 7 to 14, weight % of silver and optional promoters such as potassium, sodium, lithium, cesium and/or rubidium, generally in an amount from 0.002 to 0.08, preferably 0.003 to 0.05, weight %, on a heat-resistant, porous carrier material (all weight percentages are relative to the total catalyst). As is known, the silver is deposited in the form of metal on the internal and external surfaces of the supporting material. The morphology of the silver deposited on the supporting material can vary within wide limits. In general, it has the form of spherical particles having a diameter of 0.01 to 10 microns.

Examples of carrier materials are aluminum oxides of a very wide variety of structures, magnesium oxides, kieselguhr, pumice stone, silicon dioxide, silicon carbide, clays, corundum, zeolites, metal oxides and the like. Particularly preferred supporting materials are $\alpha$-aluminum oxides, since they have a largely uniform pore diameter. They are characterized in particular by their specific surface ($m^2/g$), their specific pore volume ($cm^3/g$) and their average pore size (micron). The supporting materials are generally employed in the form of granules, balls, rings or the like.

The process according to the invention relates to used supported silver catalysts, that is, such supported silver catalysts which have already been employed for the conversion of ethylene to ethylene oxide by means of molecular oxygen or air.

The time during which the catalyst has been in use may vary within wide limits from a few weeks to several years. In this regard, the activity of the catalyst may have declined (which generally takes place after a fairly long time of use), or the catalyst may have retained its original activity.

In the process of the invention, those used supported silver catalysts are preferably employed the activity of which has decreased, that is which belong to the so-called aged or fatigued silver catalysts. The used catalysts may contain promoters such as sodium, potassium, lithium, cesium and/or rubidium, or be free from promoters. They may have been regenerated (reactivated) once or several times according to one of the known methods, for example according to the method of German Pat. No. 2,611,856. The process of the invention is especially advantageous in the case of those aged supported silver catalysts which have been regenerated at least once, preferably 1 to 4 times, according to one of the known methods, and therefore contain cesium and/or rubidium.

The process of the invention being completed, a silver catalyst is present which generally contains 30 to 500, preferably 40 to 400, mg of cesium and/or rubidium per kg of catalyst.

The unexpected increase of activity obtained by the process of the invention cannot be explained. Obviously, the elevated impregnation temperature, as compared to usual regeneration processes, the impregnation time and the impregnating solution are acting together, and a special equilibrium between the cesium and/or rubidium concentration in the impregnating solution and that on the catalyst to be regenerated establishes itself.

As is known, the activity of a silver catalyst can be expressed as the percentage conversion of ethylene at a given reaction temperature and as the selectivity, that is the molar percentage of ethylene converted into ethylene oxide. A catalyst is the more active, the more ethylene is converted at a specific temperature, the higher the selectivity is at a specific conversion rate, and the lower the temperature is in order to achieve a specific conversion rate.

The process according to the invention considerably increases not only the selectivity of used supported silver catalysts, but also the conversion rate. It is therefore possible to reduce the reaction temperature at the same, or even a higher, conversion rate. This is particularly significant because, at a lower reaction temperature, the formation of undesirable by-products, such as carbon dioxide, formaldehyde or acetaldehyde, is considerably repressed. In view of the large quantities of ethylene oxide which are produced by the ethylene oxidation process, an increase in yield of only a few percent, or even of a tenth of a percent, acquires considerable economic importance. A factor which further distinguishes the process according to the invention is that it can be carried out in conventional large-scale manufacturing plants (using the commercially available supported silver catalysts) without an appreciable additional outlay of investment and materials.

The invention will now be illustrated in detail by means of examples according to the invention and comparative examples, which demonstrate also the critical features of the process parameters according to the invention, that is, impregnation temperature, impregnation time and water content of the impregnating solution.

The examples were carried out in a test reactor consisting of a vertically positioned reaction tube made of chrome-vanadium steel, having an inernal width of 30 mm and a length of 300 mm.

The reaction tube provided with a jacket was heated with hot oil which flowed through the jacket. The reaction tube was packed to a depth of 200 mm with $\alpha$-$Al_2O_3$ pellets; this packing served to preheat the feed gas. The catalyst to be tested rested on top of the inert packing. The feed gas entered the reaction tube (at normal pressure) from below and left it at the top.

The gas mixture employed consisted of:

| | |
|---|---|
| $C_2H_4$ | 28% by volume |
| $CH_4$ | 53% by volume |
| $O_2$ | 8% by volume |
| $CO_2$ | 5% by volume |
| $N_2$ | 6% by volume |
| Vinyl chloride | 0.0002% by volume (inhibitor). |

The space-time velocity was:

$$250 \times \frac{\text{parts by volume of gas}}{\text{hours} \times \text{parts by volume of catalyst}}$$

The temperature of the heat transfer medium was varied until a constant conversion rate of 7% of ethylene was obtained. The gas issuing at the reactor outlet was analyzed by gas chromatography, and the conversion rate and selectivity were calculated on the results obtained. Used supported silver catalysts commercially available were employed for the tests. (They consisted of about 10% of silver, particle size 1 to 5 um, on α-Al$_2$O$_3$ as supporting material, which had a specific surface of 0.1 to 0.5 m$^2$/g).

The individual catalysts used for the tests are listed as follows:

Catalyst I: is a catalyst containing no alkali metals as promoters, and was used for 7 years for the manufacture of ethylene oxide.

Catalyst II: corresponds to catalyst I with the difference, however, that after the 7 years of service it was regenerated with an impregnation solution containing cesium nitrate according to German Pat. No. 2,611,856, and subsequently served a further 2 years for the production of ethylene oxide.

Catalyst III: is a catalyst containing no alkali metals as promoters and was used for 4 years for the manufacture of ethylene oxide.

Catalyst IV: corresponds to catalyst III, with the difference, however, that it was regenerated after the 4 years of service with an impregnating solution containing cesium nitrate and ammonia according to German Offenlegungsschrift No. 2,938,245, and subsequently served a further 2 years for the production of ethylene oxide.

Catalyst V: is a catalyst which (due to its preparation according to German Offenlegungsschrift No. 2,300,512) contained cesium as promoter from the start. It was used for 2 years for the manufacture of ethylene oxide.

EXAMPLES 1 to 31

In the Examples, the catalysts I to V were tested under the conditions as indicated by means of the test reactor described above. The Examples 1 to 31 are listed individually as follows. The decisive conditions for carrying out the Examples, and the test results are summarized in a Table (the Examples not according to the invention are labelled by the addendum Comparative Example, CE).

Example 1 (Comparative Example)

Catalyst I was tested without further treatment.

Example 2 (Comparative Example)

Catalyst I was regenerated according to Example 7 of German Pat. No. 2,611,856, and then tested.

Example 3

Catalyst I was regenerated in accordance with the invention and then tested.

0.513 g of cesium nitrate were disolved in 199.5 g of distilled water. This solution was stirred into 800 g of methanol (industrial grade). The impregnating solution so obtained consisted therefore of 20 weight % of water, 350 mg of cesium (in the form of cesium nitrate) per kg of solution, that is, 0.051 weight % of cesium nitrate, and the organic solvent methanol as remainder to 100 weight % of solution, that is, 79.949 weight %.

In a 250 ml autoclave, 40 g of impregnating solution were poured over 50 g of catalyst I. The batch was heated to 100° C. and left standing at this temperature (impregnation temperature) for 5 hours. Thereafter, it was cooled, the excess impregnating solution was poured off, and the catalyst still moist was dried at 120° C. in a drying cabinet. The catalyst I so treated (regenerated) according to the invention was then tested.

Example 4 (Comparative Example)

Catalyst II was tested without further treatment.

Example 5 (Comparative Example)

Catalyst II was regenerated according to Example 10 of German Offenlegungsschrift No. 2,938,245, and then tested.

Examples 6 to 9

As described in Example 3 (according to the invention), catalyst II was regenerated at an impregnation temperature of 80° C., 100° C., 120° C. and 150° C., respectively. Each of the catalysts so obtained was tested.

Example 10

As described in Example 3, catalyst II was treated with an impregnation solution containing 250 mg of cesium per kg of solution, and tested.

Examples 11 to 15

As described in Example 3, catalyst II was treated at an impregnation time of 0.3, 1, 3, 6 and 10 hours, respectively. In Example 13, 100 mg of cesium per kg of impregnation solution were present instead of 350 mg. Each of the catalysts so obtained was tested.

Example 16

As described in Example 3, catalyst II was regenerated with the use of ethanol as organic solvent and 150 mg of cesium per kg of impregnating solution, and tested.

Example 17

As described in Example 3, catalyst II was treated with the use of isopropanol as organic solvent and 400 mg of cesium per kg of impregnating solution, and tested.

Examples 18 to 22

As described in Example 3, catalyst II was regenerated with the use of a water content in the impregnating solution of 5, 10, 20, 30 and 50 weight %, respectively, relative to the weight of the complete solution, and an impregnation time of 3 hours in each case. Each of the catalysts obtained was tested.

Example 23 (Comparative Example)

Catalyst III was tested without further treatment.

Example 24 (Comparative Example I

Catalyst III was regenerated according to Example 10 of German Offenlegungsschrift No. 2,938,245, and then tested.

Example 25

Catalyst III was regenerated as in Example 3, at an impregnation time of 3 hours, and tested.

Example 26 (Comparative Example)

Catalyst IV was tested without further treatment.

Example 27 (Comparative Example)

Catalyst IV was regenerated according to Example of German Offenlegungsschrift No. 2,938,245, and then tested.

Example 28

Catalyst IV was regenerated as in Example 3 at an impregnation time of 3 hours, and tested.

Example 29 (Comparative Example)

Catalyst V was tested without further treatment.

Example 30

Catalyst V was regenerated as in Example 3 at an impregnation time of 3 hours, and tested.

Example 31

As described in Example 3, catalyst V was regenerated with the use of cesium acetate at an impregnation time of 3 hours, and tested.

hours with an impregnating solution containing water, a water-miscible organic solvent selected from the group consisting of methanol, ethanol, propanol, and isopropanol, at least one compound of cesium, rubidium, or of cesium and rubidium in an amount providing from 50 mg to 1000 mg per kilogram of solution, said solution containing from 5 to 50 percent by weight of water;
(b) separating the impregnated catalyst from excess impregnating solution; and
(c) drying the impregnated catalyst.

2. A method as in claim 1 wherein said used catalyst is impregnated at a temperature from 90°0 C. to 130° C.

3. A method as in claim 1 wherein said used catalyst is impregnated for 1 hour to 3 hours.

4. A method as in claim 1 wherein said impregnating

TABLE

CONDITIONS OF REGENERATION

| Example No. (CE = comparative Example) | Composition of impregnating solution | | | | | Temperature (°C.) | Time (h) | Results of regeneration | |
|---|---|---|---|---|---|---|---|---|---|
| | Solvent | Water amount (weight %) | Cesium compound | mg Cs per kg solution | Cs compound in solution (weight %) | | | Temperature for 7% $C_2H_4$ conversion | Selectivity at 7% $C_2H_4$ conversion |
| 1 CE | | | | | | | | 260 | 68.5 |
| 2 CE | | | | | | | | 230 | 77.0 |
| 3 | $CH_3OH$ | 20 | $CsNO_3$ | 350 | 0.051 | 100 | 5 | 225 | 77.7 |
| 4 CE | | | | | | | | 242 | 72.0 |
| 5 CE | | | | | | | | 228 | 77.5 |
| 6 | $CH_3OH$ | 20 | $CsNO_3$ | 350 | 0.051 | 80 | 5 | 223 | 77.7 |
| 7 | $CH_3OH$ | 20 | $CsNO_3$ | 350 | 0.051 | 100 | 5 | 220 | 78.1 |
| 8 | $CH_3OH$ | 20 | $CsNO_3$ | 350 | 0.051 | 120 | 5 | 219 | 78.2 |
| 9 | $CH_3OH$ | 20 | $CsNO_3$ | 350 | 0.051 | 150 | 5 | 219 | 78.2 |
| 10 | $CH_3OH$ | 20 | $CsNO_3$ | 250 | 0.037 | 100 | 5 | 220 | 78.0 |
| 11 | $CH_3OH$ | 20 | $CsNO_3$ | 350 | 0.051 | 100 | 0.3 | 226 | 77.7 |
| 12 | $CH_3OH$ | 20 | $CsNO_3$ | 350 | 0.051 | 100 | 1 | 220 | 78.0 |
| 13 | $CH_3OH$ | 20 | $CsNO_3$ | 100 | 0.015 | 100 | 3 | 220 | 78.2 |
| 14 | $CH_3OH$ | 20 | $CsNO_3$ | 350 | 0.051 | 100 | 6 | 220 | 78.3 |
| 15 | $CH_3OH$ | 20 | $CsNO_3$ | 350 | 0.051 | 100 | 10 | 220 | 78.3 |
| 16 | $C_2H_5OH$ | 20 | $CsNO_3$ | 150 | 0.022 | 100 | 5 | 219 | 78.2 |
| 17 | $i\text{-}C_3H_7OH$ | 20 | $CsNO_3$ | 400 | 0.059 | 100 | 5 | 220 | 78.1 |
| 18 | $CH_3OH$ | 5 | $CsNO_3$ | 350 | 0.051 | 100 | 3 | 225 | 77.7 |
| 19 | $CH_3OH$ | 10 | $CsNO_3$ | 350 | 0.051 | 100 | 3 | 222 | 78.2 |
| 20 | $CH_3OH$ | 20 | $CsNO_3$ | 350 | 0.051 | 100 | 3 | 220 | 78.3 |
| 21 | $CH_3OH$ | 30 | $CsNO_3$ | 350 | 0.051 | 100 | 3 | 220 | 78.2 |
| 22 | $CH_3OH$ | 50 | $CsNO_3$ | 350 | 0.051 | 100 | 3 | 230 | 78.0 |
| 23 CE | | | | | | | | 260 | 68.0 |
| 24 CE | | | | | | | | 228 | 77.4 |
| 25 | $CH_3OH$ | 20 | $CsNO_3$ | 350 | 0.051 | 100 | 3 | 219 | 78.3 |
| 26 CE | | | | | | | | 245 | 73.0 |
| 27 CE | | | | | | | | 227 | 77.3 |
| 28 | $CH_3OH$ | 20 | $CsNO_3$ | 350 | 0.051 | 100 | 3 | 220 | 77.9 |
| 29 CE | | | | | | | | 235 | 75.0 |
| 30 | $CH_3OH$ | 20 | $CsNO_3$ | 350 | 0.051 | 100 | 3 | 217 | 78.2 |
| 31 | $CH_3OH$ | 20 | $CsOOCH_3$ | 350 | 0.050 | 100 | 3 | 221 | 78.1 |

What is claimed is:

1. A method for improving the activity of a used supported silver catalyst, used for the manufacture of ethylene oxide by reaction of ethylene with oxygen or air, which method consists essentially of:
    (a) impregnating said used catalyst at a temperature from 80° C. to 150°0 C. and for 0.75 hour to 10 solution contains from 10 to 40 percent by weight of water.

5. A method as in claim 4 wherein said impregnating solution contains from 10 to 30 percent by weight of water.

* * * * *